US012723224B2

(12) United States Patent
Schober et al.

(10) Patent No.: US 12,723,224 B2
(45) Date of Patent: Sep. 1, 2026

(54) METHOD FOR THREE-DIMENSIONAL REPLICATION OF A BIOLOGICAL TISSUE

(71) Applicant: Technische Universität Ilmenau, Ilmenau (DE)

(72) Inventors: Andreas Schober, Erfurt (DE); Frank Weise, Ilmenau (DE); Jörg Hampl, Erfurt (DE); Dana Brauer, Elgersburg (DE)

(73) Assignee: Technische Universität Ilmenau, Ilmenau (DE)

( * ) Notice: Subject to any disclaimer, the term of this patent is extended or adjusted under 35 U.S.C. 154(b) by 642 days.

(21) Appl. No.: 18/129,112

(22) Filed: Mar. 31, 2023

(65) Prior Publication Data

US 2023/0313093 A1 Oct. 5, 2023

(30) Foreign Application Priority Data

Apr. 4, 2022 (DE) ..................... 10 2022 108 006.4

(51) Int. Cl.
*C12M 3/06* (2006.01)
*C12M 3/00* (2006.01)

(52) U.S. Cl.
CPC ............ *C12M 21/08* (2013.01); *C12M 23/16* (2013.01)

(58) Field of Classification Search
None
See application file for complete search history.

(56) References Cited

U.S. PATENT DOCUMENTS

| | | | |
|---|---|---|---|
| 2005/0169962 A1 | 8/2005 | Bhatia | |
| 2007/0081983 A1* | 4/2007 | Andreadis | A61L 27/3808 435/366 |
| 2015/0118197 A1 | 4/2015 | Claeyssens | |
| 2017/0196818 A1* | 7/2017 | Shin | A61K 35/12 |
| 2019/0017999 A1* | 1/2019 | Jeon | C12N 5/0629 |
| 2020/0113837 A1* | 4/2020 | Karumbaiah | A61K 35/30 |
| 2022/0054639 A1* | 2/2022 | Yang | A61K 9/0019 |

FOREIGN PATENT DOCUMENTS

| | | |
|---|---|---|
| DE | 102010037968 A1 | 4/2012 |
| DE | 102015122375 A1 | 12/2016 |
| WO | 2011/035937 A1 | 3/2011 |
| WO | 2017/153947 A1 | 9/2017 |

OTHER PUBLICATIONS

Gong & Mills "Large-scale patterning of single cells and cell clusters in hydrogels" (2018), Sci Rep, 8: 3849. (Year: 2018).*
Ravanbakhsh et al. "Emerging Technologies in Multi-Material Bioprinting" (2021), Adv Mat. vol. 33, No. 49, 2104730 (Year: 2021).*
Author Unknown "Printing System Autodrop Compact AD-P-7000" product data sheet from microdrop Technologies GmbH, Norderstedt, Germany, Feb. 2021, 2 pages.
Gao, et al. "Advanced Strategies for 3D Bioprinting of Tissue and Organ Analogs Using Alginate Hydrogel Bioinks" in Marine Drugs, 2021, 19, 708.
Jeong, et al., "3D Bioprinting Strategies for the Regeneration of Functional Tubular Tissues and Organs" in Bioengineering, Basel, 2020, 7, 32.
Hati, et al. "Versatile, cell and chip friendly method to gel alginate in microfluidic devices" in Lab on a Chip, 2016. 16 (19), pp. 3718-3727.
Bassett, et al. "Competitive ligand exchange of crosslinking ions for ionotropic hydrogel formation" in the Journal of Material Chemistry B, 2016. 4(37), pp. 6175-6182.
Murphy et al. "3D bioprinting of tissues and organs" in Nature Biotechnology, 2014. 32(8), pp. 773-785.
Gerecht et al: "Hyaluronic acid hydrogel for controlled self-renewal and differentiation of human embryonic stem cells" in PNAS, Issue 104, No. 27, pp. 11298-11303, Jul. 2007.
Chan et al: "Three-dimensional photo-patterning of hydrogels using stereolithography for long-term cell encapsulation" in Lab on a Chip, 2010, issue 10, pp. 2062-2070.
Ye et al: "Hydrogels for Liver Tissue Engineering" in Bioengineering 2019, 6, 59, doi:10.3390/bioengineering6030059, pp. 1 to 30.

* cited by examiner

*Primary Examiner* — Teresa E Knight
(74) *Attorney, Agent, or Firm* — Kaplan Breyer Schwarz LLP

(57) ABSTRACT

A method for three-dimensional reproduction of a biological tissue in the framework of tissue engineering. A substrate is provided and primary cells of a first cell type are deposited on the substrate. A first precursor of a substance adhering the cells is arranged on at least a selection of the primary cells of the first cell type. A second precursor of the substance adhering the cells is arranged in a locally targeted manner on the selection of primary cells of the first cell type according to a structure formed by cells of the first cell type in the tissue to be reproduced. The first precursor and the second precursor react with each other to form the substance adhering the cells, which substance adheres the selection of the primary cells of the first cell type according to the structure formed by the cells of the first cell type in the tissue to be reproduced.

15 Claims, 6 Drawing Sheets

Y
X
07
09
06
01
02
03
08
04

Y
X
09
11
12
06
01
02
03
08
04

METHOD FOR THREE-DIMENSIONAL REPLICATION OF A BIOLOGICAL TISSUE

BACKGROUND OF THE INVENTION

The present invention relates to a method for three-dimensional reproduction of a biological tissue in the framework of tissue engineering.

The article by S. V. Murphy and A. Atala: "3D bioprinting of tissues and organs" in Nature Biotechnology, 2014. 32(8), pages 773-785 illustrates the use of 3D printing techniques for the fabrication of biocompatible materials, cells, and supporting components for complex living 3D functional tissues.

The article by D. C. Bassett, A. G. Hati, T. B. Melo, B. T. Stokke and P. Sikorski: "Competitive ligand exchange of crosslinking ions for ionotropic hydrogel formation" in the Journal of Material Chemistry B, 2016. 4(37), pages 6175-6182 describes an approach to form hydrogels from ionotropic polymers by competitive displacement of chelated ions.

The article by A. G. Hati, D. C. Bassett, J. M. Ribe, P. Sikorski et al: "Versatile, cell and chip friendly method to gel alginate in microfluidic devices" in Lab on a Chip, 2016. 16(19), pages 3718-3727 describes the use of alginate in microfluidic devices to produce discrete beads or fibers in micro-scale. Such structures can be used to encapsulate sensitive cells and biomolecules.

The company ClexBio/Nordovo Biosciences AS, Oslo, Norway offers a two-component hydrogel under the product name "Clex".

WO 2017/153947 A1 discloses a method for the formation of a crosslinked polymer hydrogel using competitive ligand exchange. In this method, a first solution and a second solution are mixed. The first solution comprises a crosslinking agent and a first chelating agent. The second solution comprises a displacement agent. At least one of the two solutions comprises an ionotropic polymer.

The article by H.-J. Jeong, H. Nam, J. Jang and S.-J. Lee: "3D Bioprinting Strategies for the Regeneration of Functional Tubular Tissues and Organs" in Bioengineering, Basel, 2020, 7, 32, describes the use of 3D bioprinting technology for the fabrication of patient-specific and complex-shaped free-form architectures.

The article by Q. Q. Gao, B.-S. Kim and G. Gao: "Advanced Strategies for 3D Bioprinting of Tissue and Organ Analogs Using Alginate Hydrogel Bioinks" in Marine Drugs, 2021, 19, 708, demonstrates the use of natural polysaccharide alginate as a bioink source for 3D bioprinting.

The "Printing System Autodrop Compact AD-P-7000" product data sheet from microdrop Technologies GmbH, Norderstedt, Germany, describes a drop-on-demand system with a piezo-driven dispenser.

WO 2011/035937 A1 describes a micro-structured molded body comprising a film divided into undeformed regions and thinned stretching regions. Micro-structures are formed in at least some of the thinned stretching regions, wherein pores are formed in at least one of the thinned stretching regions.

Furthermore, a micro-structured molded body is known from WO 2011/035938 A1, which has a film-like base body which comprises a first film layer and a second film layer located thereunder, wherein the second film layer has recesses with a diameter of less than 2 mm, which recesses are formed by deformed regions of the first film layer, through which cavities are formed. At least some of the deformed areas of the first film layer have pores.

DE 10 2010 037 968 A1 describes a structure for simulating a sinusoid that can be inserted into a microtiter plate. The structure comprises a plurality of layers of porous material arranged one above the other, wherein an intermediate space is respectively formed between the layers. The intermediate spaces are connected by channels formed in the layers for conveying a fluid.

DE 10 2015 122 375 A1 relates to a method for reproducing a stem cell niche of an organism. An image of a tissue of an organism comprising at least one stem cell niche is generated. The image is filtered to obtain a structural pattern of the imaged stem cell niche. In a further step, a lithographic mask is generated from the structural pattern. A starting material of a substrate is structured by means of indirect or direct application of the lithographic mask, whereby a structured substrate is obtained which constitutes the reproduction of the imaged stem cell niche of the organism.

An overview of the use of hydrogels for reproduction of stem cell niches can be found in the article by S. Gerecht et al: "Hyaluronic acid hydrogel for controlled self-renewal and differentiation of human embryonic stem cells" in PNAS, Issue 104, No. 27, pages 11298-11303, July 2007.

In the article by V. Chan et al: "Three-dimensional photopatterning of hydrogels using stereolithography for long-term cell encapsulation" in Lab on a Chip, 2010, issue 10, pages 2062-2070, a method for polymerization of hydrogels is described for which the light of a UV laser is used. The polymerized hydrogels form structures for cells.

US 2015/0118197 A1 discloses a method for the fabrication of an electrospun scaffold by which, for example, the morphology of a niche in the palisades of Vogt of a limbus can be reproduced.

US 2005/0169962 A1 discloses a method for the fabrication of patterned three-dimensional biopolymer scaffolds with living cells. The method involves the selective photopolymerization of biopolymers to create patterned structures and patterning of cells within relatively homogeneous biopolymer sheets using dielectrophoresis.

In the article by S. Ye et al: "Hydrogels for Liver Tissue Engineering" in Bioengineering 2019, 6, 59, doi:10.3390/bioengineering6030059, pages 1 to 30, a method for bioengineering liver tissue is described. The use of various hydrogels is explained.

A disadvantage of prior art methods for reproduction of biological tissues is that the cells to be embedded are subjected to stresses that have a negative impact on the vitality of the cells. Cells are subjected to high compressive and shear forces to achieve the desired local resolution in 3D printing for reproduction of biological tissues. If one reduces the local resolution, then the reproduction of the biological tissue does not succeed sufficiently. If the principle of photopolymerization is used, the cells are exposed to harmful UV radiation.

Starting from the prior art, the task of the present invention is to enable a three-dimensional reproduction of biological tissues in which the cells to be embedded are not exposed to any stresses that are harmful to the cells.

Said task is solved by a method according to the appended claim 1.

SUMMARY OF THE INVENTION

The method according to the invention is used for the three-dimensional reproduction of a biologically natural tissue. The biological tissue is preferably a biological tissue of an organism. The organism is preferably a living organism in which the tissue is formed. The living organism is in particular an animal or a human being. The biological tissue is, for example, a tissue of a liver of a human or an animal. The tissue to be reproduced is, for example, formed by hepatic tissue. As a result of the method according to the invention, a reproduction of the biological tissue is obtained, wherein the reproduction reproduces at least a part of the biological tissue in three dimensions. The reproduction at least partially reproduces the morphology and functions of the biological tissue. Preferably, the reproduction substantially completely reproduces the morphology and functions of the biological tissue. The reproduction preferably reproduces a section of an organ or an organ. In this sense, the reproduction constitutes an organotypic oligocellular 3-dimensional tissue construct.

In one step of the method, a substrate is provided which serves as a base for the build-up of the reproduction. The substrate is preferably biocompatible. The substrate is preferably planar or alternatively preferably three-dimensionally shaped to contribute to the three-dimensional reproduction of the tissue.

In a further step, primary cells of a first cell type are deposited at least on the substrate. Through the deposit of the primary cells, the cells are arranged on the substrate. The primary cells of the first cell type are preferably deposited locally in an undirected and unstructured manner on the substrate, such that they do not have any order and in this respect do not yet reproduce the morphology of the tissue to be reproduced. The primary cells of the first cell type are preferably deposited or alternatively arranged uniformly stochastically distributed on the substrate. Preferably, the deposit of the primary cells takes place by means of pipetting. The primary cells of the first cell type are preferably prepared before being deposited on the substrate by taking them from a sample of the tissue to be reproduced.

In a further step, a first precursor of a substance adhering the cells to be formed later is arranged on at least a selection of the primary cells of the first cell type. The first precursor is a first chemical or biochemical starting material which is required in order to form the substance adhering the cells by a chemical reaction. The substance adhering the cells to be formed will be suitable to mechanically connect, by adhesion forces, those primary cells of the first cell type upon which this substance is formed, whereby their relative positions to each other and to the substrate are fixed.

In a further step, a second precursor of the substance adhering the cells is selectively arranged on the selection of primary cells of the first cell type according to a structure formed by cells of the first cell type in the natural tissue to be reproduced. This arrangement is preferably performed with a locally metering dispensing system, such as a dispensing or pipetting system that is movable in the x-y axes, or preferably a dispensing or pipetting system movable in the x-y-z axes. A starting point for this step is the structure formed by the cells of the first cell type in the tissue to be reproduced. This structure describes the local three-dimensional arrangement of the cells of the first cell type in the tissue to be reproduced. Since this structure serves as a template for the targeted local arrangement of the second precursor of the substance adhering the cells on the selection of the primary cells of the first cell type, a morphological reproduction of the tissue to be reproduced is carried out. By the local arrangement of the second precursor, the first precursor and the second precursor react with each other at these locations such that they there form the substance adhering the cells, whereupon this substance adheres the selection of primary cells of the first cell type to each other according to the structure formed by the cells of the first cell type in the tissue to be reproduced. Preferably, the selection of primary cells of the first cell type is also simultaneously adhered to the substrate. The second precursor can only react chemically with the first precursor and form the substance adhering the cells where it is selectively locally arranged, such that only there will the primary cells of the first cell type adhere. The now adhered primary cells of the first cell type of said selection reproduce at least a first section of the biological tissue to be reproduced, such that they constitute a reproduction of at least this first section. This reproduction preferably forms a first layer of the primary cells. The structure determining spatial arrangement and distribution of the selection of primary cells is fixed by the adhesive substance. This spatial arrangement and distribution are a copy of the spatial arrangement and distribution of the primary cells in the natural tissue to be reproduced. The three-dimensional structure of the primary cells of the first cell type in the natural tissue to be reproduced serves as a template, such that a description of this structure is required. To the extent that this description is not already known by those skilled in the art, the natural tissue to be reproduced can be examined to obtain a description of this structure.

A particular advantage of the method according to the invention is that the selection of the primary cells undergoes a local arrangement according to the structure of the natural tissue to be reproduced, without having to be moved locally in a targeted manner. In particular, the primary cells do not need to be arranged with a dispenser working in a locally targeted manner, which would subject the primary cells to high shear forces, which would have a detrimental effect on their service life. A further advantage is that no radiation is required to form the substance adhering the cells, since this substance is formed by the amalgamation of the first precursor with the second precursor. Such radiation would also have a detrimental effect on the service life of the cells.

In preferred embodiments, the substrate to be provided comprises microfluidic structural elements. The microfluidic structural elements preferably reproduce a microfluidic structure of the biological tissue to be reproduced. The microfluidic structural elements are at least configured, also in the reproduction, to functionally enable microfluidic processes which occur in the biological tissue to be reproduced. The microfluidic structural elements are preferably formed by openings, holes, trenches, channels and/or porous sections in the substrate. Moreover, the substrate preferably has cavities and/or elevations, which also serve for the three-dimensional reproduction of the biological tissue to be reproduced.

The substrate preferably consists of a polymer, which is preferably biocompatible. The substrate is preferably formed by a film.

The substrate is preferably formed by a microtiter plate or by a microstructured molded body. The substrate is preferably at least 10 mm long and at least 10 mm wide.

The substance adhering the cells is preferably formed by a hydrogel, which is preferably a crosslinked polymer hydrogel. The substance adhering the cells is preferably formed by a two-component hydrogel. In this case, the first precursor constitutes a first component of the two-component hydrogel. The second precursor constitutes a second component of the two-component hydrogel. The first precursor and the second precursor are preferably each in the form of a solution. The formation of the substance adhering the cells from the first precursor and the second precursor preferably involves a competitive ligand exchange. The formation of the substance adhering the cells from the first precursor and the second precursor requires a period of time, which constitutes, in particular, a gelation time and which is preferably less than 1 second, further preferably less than 100 ms and particularly preferably less than 10 ms. The gelation time is preferably less than a dissipation time, such that a functional fixation of the cells of the first cell type occurs. One of the two precursors preferably comprises a crosslinking agent and a first chelating agent, whereas the other of the two precursors comprises a displacement agent. One of the two precursors preferably comprises an ionotropic polymer. The ionotropic polymer is preferably formed by alginate, pectin, poly(galacturonate), carrageenan, dextran, gellan, scleroglucan, chitosan, polyphosphazene, sodium polyacrylate and/or polyamino acid. The ionotropic polymer is particularly preferably formed by alginate. In principle, the substance adhering the cells can also consist of another gel or adhesive.

In preferred embodiments, the primary cells of the first cell type are deposited in a medium, in particular in a liquid medium. The medium can be arranged on the substrate before the primary cells of the first cell type are deposited. However, the medium can also be arranged on the substrate together with the primary cells of the first cell type. Preferably, the medium is arranged on the substrate by pipetting. Particularly preferably, however, the substrate is arranged in the medium and the primary cells of the first cell type are deposited in the medium on the substrate. The medium preferably comprises at least one nutrient medium for the primary cells of the first cell type, such that the primary cells of the first type are nourished in the following. The medium is found at least on the substrate, wherein it is preferably arranged at least where the primary cells of the first cell type are also arranged.

In preferred embodiments, the medium comprises the first precursor of the substance adhering the cells or the first precursor is mixed into the medium present on the substrate. In these embodiments, the first precursor is preferably arranged in a locally non-targeted manner in a selection of the primary cells of the first cell type such that the first precursor is found at all primary cells of the first cell type that are deposited. Since both of the precursors are required to form the substance adhering the cells, the substance adhering the cells is anyway only formed where the second precursor is arranged in a locally targeted manner. The medium correspondingly preferably comprises the culture medium and the first precursor. In alternatively preferred embodiments, the first precursor is also arranged in a locally targeted manner according to the structure formed by the cells of the first cell type in the tissue to be reproduced. This arrangement is preferably carried out with a locally metering dispensing system, such as a dispensing or pipetting system movable in the x-y axes or preferably a dispensing or pipetting system movable in the x-y-z axes. In this manner, both precursors are arranged at the same locations, where they form the substance adhering the cells. The first precursor and the second precursor can be arranged in a targeted manner in succession or simultaneously.

In principle, the first precursor can be arranged before or after the second precursor or simultaneously with the second precursor at or alternatively on the primary cells of the first cell type.

The second precursor of the substance adhering the cells is preferably arranged at or alternatively on the selection of primary cells of the first cell type using a locally targeted dispenser or pipetting system. Thereby, the second precursor is arranged in single drops at or alternatively on the selection of primary cells of the first cell type, wherein the smallest dispensable drops preferably contain at most 5 picoliters of the second precursor and further preferably at most 1 picoliter of the second precursor. During the arrangement in a locally targeted manner of the second precursor, travel distances are preferably covered in all three spatial axes, the travel distances preferably being at least 10 mm and further preferably at least 100 mm. The locally targeted arrangement takes place with an accuracy of ±100 μm or better. This accuracy is further preferably ±25 μm or better.

The dispensing system working in a locally targeted manner preferably comprises a 3D printer with a dispensing head, which is preferably based on inkjet technology. The dispensing head is configured for locally targeted dispensing of the second precursor. The dispenser preferably forms a drop-on-demand system. The locally targeted dispensing or alternatively pipetting system preferably comprises a plurality of drives for driving the dispensing head or alternatively the pipette in a plurality of spatial axes to locally target the second precursor on the selection of primary cells of the first cell type according to the structure formed by the cells of the first cell type in the tissue to be reproduced. The dispensing head or alternatively pipette can preferably be moved in all three spatial axes using the travel path methods described above.

After the first precursor and the second precursor have formed the substance adhering the cells, those remaining primary cells of the first cell type that do not belong to the selection initially remain loose on the substrate, since they are not locally fixed by the substance adhering the cells. Only the primary cells of the first cell type belonging to the selection reproduce the said first section of the biological tissue to be reproduced, since only these primary cells are arranged according to the structure formed by the cells of the first cell type in the tissue to be reproduced. The remaining primary cells are loosely arranged outside this structure and, at least in this method phase, are no longer required, such that they are preferably removed from the substrate, which can, for example, occur by means of a washing process. Preferably, the removal of the remaining primary cells is carried out by pipetting. In those embodiments in which the first precursor has not been locally targeted, remainders of the first precursor also remain on those primary cells of the first cell type that are not part of the selection. These remainders of the first precursor are in any case no longer required in this method phase, so that they are preferably removed from the substrate together with the remaining loose primary cells of the first cell type. The removed primary cells of the first cell type and the removed remainders of the first precursor are, however, preferably reused for later steps of the method.

In preferred embodiments, in addition to the first section that reproduces the tissue, at least one further section of the tissue is reproduced. The reproduction of the further section can be formed by further primary cells of the first cell type or by primary cells of a second cell type to create a co-culture. In the first case, the steps of the deposit of primary cells of the first cell type, the arrangement of the first precursor and the arrangement in a locally targeted manner of the second precursor are repeated. In this manner, further primary cells of the first cell type are initially deposited or alternatively arranged on the already formed reproduction of the first section of the biological tissue. The first precursor of the substance adhering the cells is arranged at or alternatively on at least one selection of the further primary cells of the first cell type. An arrangement in a locally targeted manner of the second precursor of the substance adhering the cells at or alternatively on the selection of further primary cells of the first cell type according to the structure formed by cells of the first cell type in the tissue to be reproduced takes place. The first precursor and the second precursor are amalgamated and chemically react with each other to form the substance adhering the cells, which substance adheres the selection of further primary cells of the first cell type according to the structure formed by cells of the first cell type in the tissue to be reproduced, such that the selection of further primary cells of the first cell type reproduces the second section of the biological tissue to be reproduced, whereby they constitute a reproduction of this further section. In this regard, the selection of the further primary cells of the first cell type is simultaneously at least partially adhered to the reproduction of the first section of the biological tissue. The reproduction of the further section of the biological tissue to be reproduced preferably forms a second layer of the primary cells.

In embodiments in which the reproduction of the further section is to be formed by primary cells of the second cell type, primary cells of the second cell type are first deposited or alternatively arranged on the substrate and/or on the already formed reproduction of the first section of the biological tissue. The first precursor of the substance adhering the cells is arranged at or alternatively on at least one selection of primary cells of the second cell type. The second precursor of the substance adhering the cells is arranged in a locally targeted manner at or alternatively on the selection of primary cells of the second cell type according to a structure formed by cells of the second cell type in the tissue to be reproduced. The first precursor and the second precursor are amalgamated and chemically react with each other, such that they form the substance adhering the cells, which substance adheres the selection of primary cells of the second cell type according to the structure formed by cells of the second cell type in the tissue to be reproduced, such that the selection of primary cells of the second cell type reproduces the second section of the biological tissue to be reproduced, whereby they reproduce a reproduction of this further section. In this regard, the selection of primary cells of the second cell type is simultaneously adhered to the substrate and/or at least partially adhered to the reproduction of the first section of the biological tissue. The reproduction of the further section of the biological tissue to be reproduced preferably forms a second layer of primary cells or alternatively a first layer of the primary cells of the second cell type.

The steps of the deposit of the further primary cells of the first cell type or alternatively the primary cells of the second cell type, the subsequent arrangement of the first precursor and the arrangement in a locally targeted manner of the second precursor are preferably carried out according to the preferred embodiments described above concerning the deposit of the primary cells of the first cell type and the subsequent arrangement of the first precursor and the arrangement in a locally targeted manner of the second precursor.

In further preferred embodiments, additional sections of the tissue are reproduced. For reproductions of the further sections, primary cells of a third and/or a further cell type are preferably also used.

In preferred embodiments, at least five of the sections of biological tissue are reproduced such that the reproduction comprises at least five of the layers of primary cells of one or more cell types.

A reproduction of a biological tissue can be fabricated by the method according to the invention. The reproduction can preferably be fabricated by one of the described preferred embodiments of the method according to the invention. The reproduction, moreover, preferably also has such features as are described in connection with the method according to the invention.

BRIEF DESCRIPTION OF THE DRAWINGS

Further advantages, details and further developments of the invention will be apparent from the following description of preferred embodiments of the invention, with reference to the drawing. Wherein.

DETAILED DESCRIPTION OF THE INVENTION

Figures 1, 2:
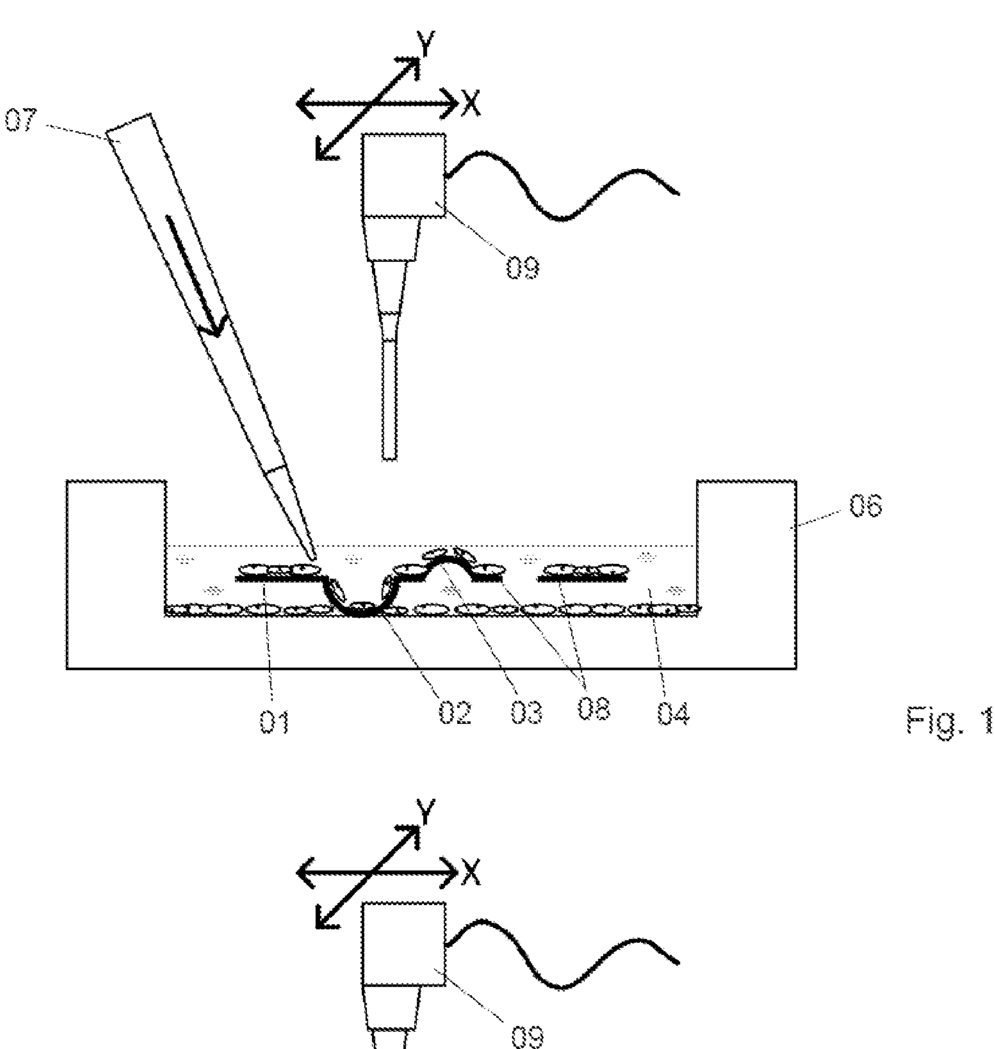
FIG. 1: shows a first phase of a first preferred embodiment of a method according to the invention for reproduction of biological tissue.
FIG. 2: shows a second phase of the first preferred embodiment of the method according to the invention.

FIG. 1 shows a first phase of a first preferred embodiment of a method for the reproduction of biological tissue according to the invention. A structured substrate 01 in the form of a film with cavities 02 and elevations 03 is provided and arranged in a medium 04 in a machining tray 06. Using a pipette 07, primary cells 08 of a first cell type are deposited on the substrate 01. In this manner, some of the primary cells 08 of the first cell type do not remain on the substrate 01 but rather reach a bottom of the machining tray 06. The primary cells 08 of the first cell type are distributed in a locally untargeted manner over the substrate 01 using the pipette 07 such that the primary cells 08 are distributed in a largely uniform manner. When the primary cells 08 of the first cell type are deposited with the pipette 07, the primary cells 08 are not subjected to high compressive or shear stress. A dispensing system 09, which is movable in x-y axes and is not yet used in this first phase, is arranged above the machining tray 06. The dispensing system 09 can preferably also be configured in the method in the three x-y-z axes or can also be formed by a pipetting system.

The medium 04 comprises a first precursor for a later to be formed substance 11 to adhere the primary cells 08

(shown in FIG. 2). The medium 04 moreover comprises a nutrient medium for the primary cells 08 of the first cell type.

FIG. 2 shows a second phase of the first preferred embodiment of the method for the reproduction of biological tissue according to the invention. In this second phase, the dispensing system 09, which can be moved in the x-y axes, is used to selectively arrange a second precursor 12 of the substance 11 that adheres the cells 08 on a selection of the primary cells 08 of the first cell type. The second precursor 12 is arranged in a locally targeted manner according to a structure actually formed by the cells 08 of the first cell type in the tissue to be reproduced (not shown). The first precursor that is present in the medium 04 and the second precursor 12 immediately form the substance 11 in the form of a hydrogel adhering the cells 08. The adhered selection of primary cells 08 of the first cell type constitutes a reproduction of a first section of the biological tissue to be reproduced (not shown).

Figure 3:
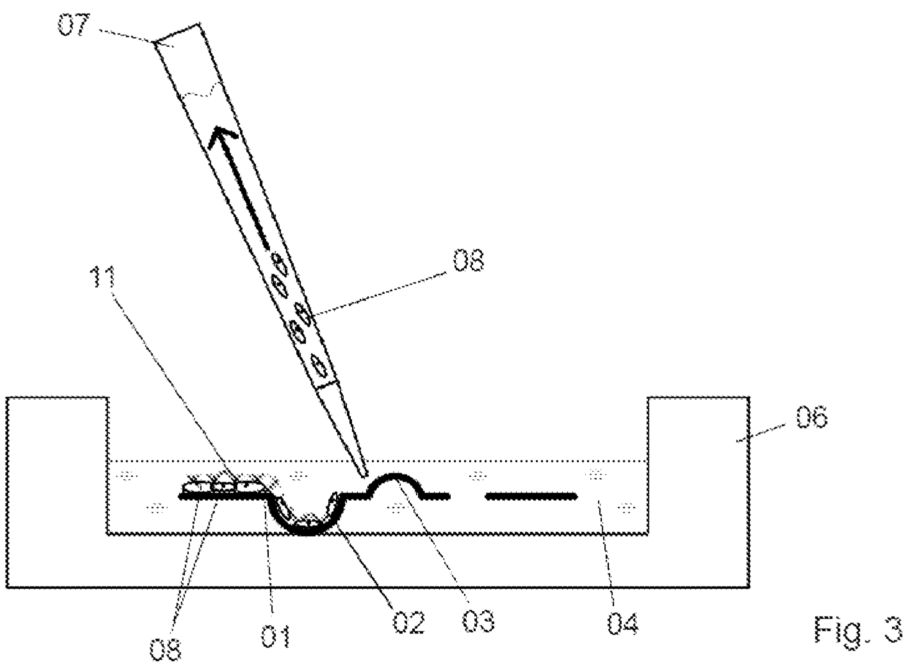
FIG. 3: shows a third phase of the first preferred embodiment of the method according to the invention.

FIG. 3 shows a third phase of the first preferred embodiment of the method for the reproduction of biological tissue according to the invention. In this third phase, the primary cells 08 of the first cell type that are not adhered by the substance 11 are removed from the substrate 01 and from the medium 04 using the pipette 07.

Figure 4:
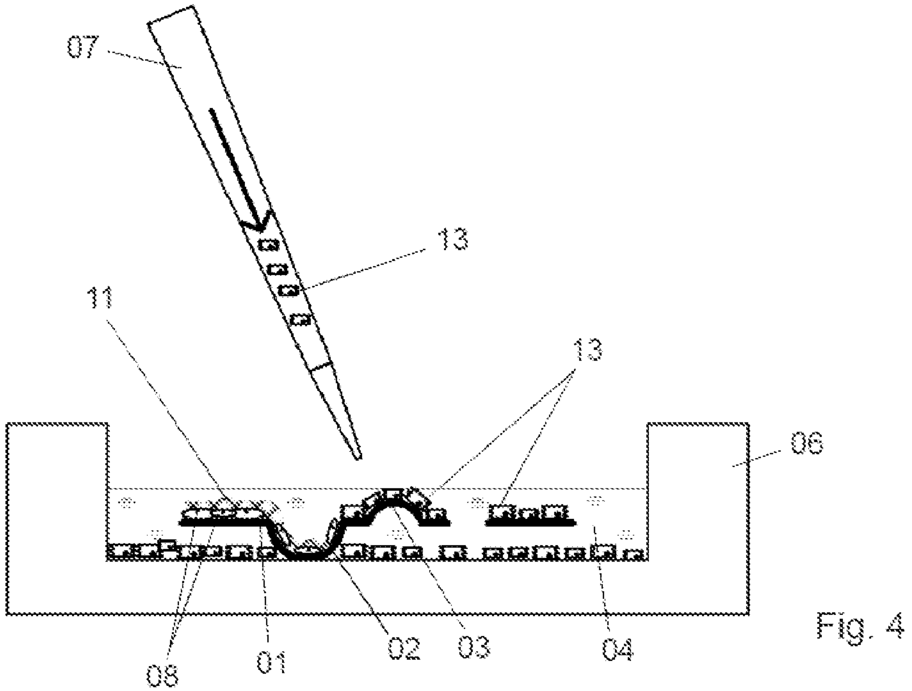
FIG. 4: shows a fourth phase of the first preferred embodiment of the method according to the invention.

FIG. 4 shows a fourth phase of the first preferred embodiment of the method for the reproduction of biological tissue according to the invention. The pipette 07 is now used to deposit primary cells 13 of a second cell type on the substrate 01. In this manner, some of the primary cells 13 of the second cell type do not remain on the substrate 01 but rather reach the bottom of the machining tray 06. The primary cells 13 of the second cell type are distributed in a locally untargeted manner over the substrate 01 with the pipette 07, such that the primary cells 13 are distributed in a largely uniform manner. When the primary cells 13 of the second cell type are deposited with the pipette 07, the primary cells 13 are not subjected to high compressive or shear stress.

Figure 5:
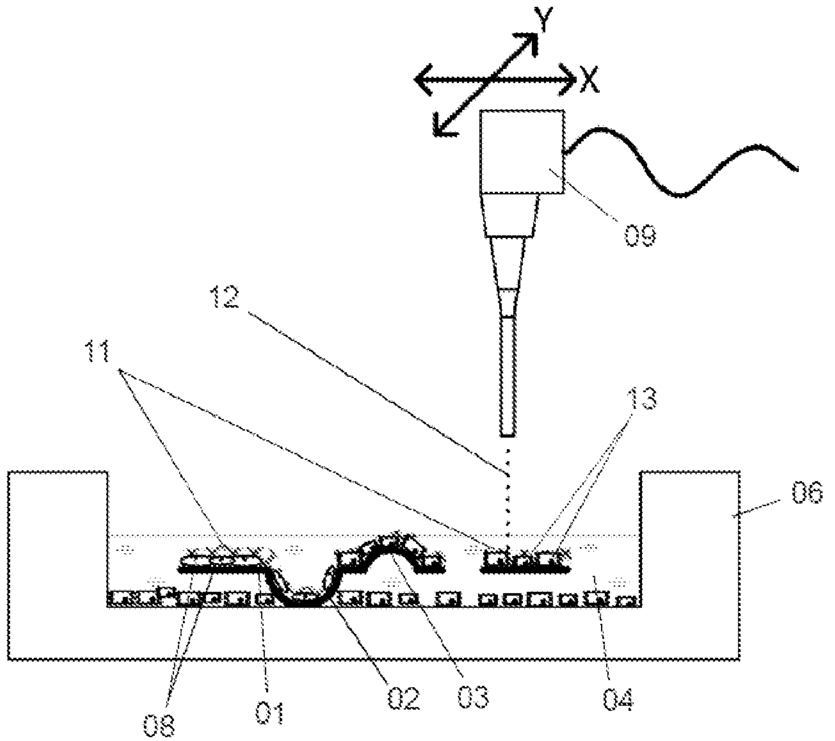
FIG. 5: shows a fifth phase of the first preferred embodiment of the method according to the invention.

FIG. 5 shows a fifth phase of the first preferred embodiment of the method for the reproduction of biological tissue according to the invention. In this fifth phase, the dispensing system 09, which can be moved in the x-y axes, is used to selectively arrange in a locally targeted manner further amounts of the second precursor 12 of the substance 11 adhering the cells 08, 13 on a selection of the primary cells 13 of the second cell type. The second precursor 12 is arranged in a locally targeted manner according to a structure actually formed by the cells 13 of the second cell type in the tissue to be reproduced (not shown). The first precursor that is present in the medium 04 and the second precursor 12, in turn, immediately form the substance 11, in the form of a hydrogel, adhering the cells 08, 13. The adhered selection of primary cells 13 of the second cell type constitutes a reproduction of a second section of the biological tissue to be reproduced (not shown).

Figure 6:
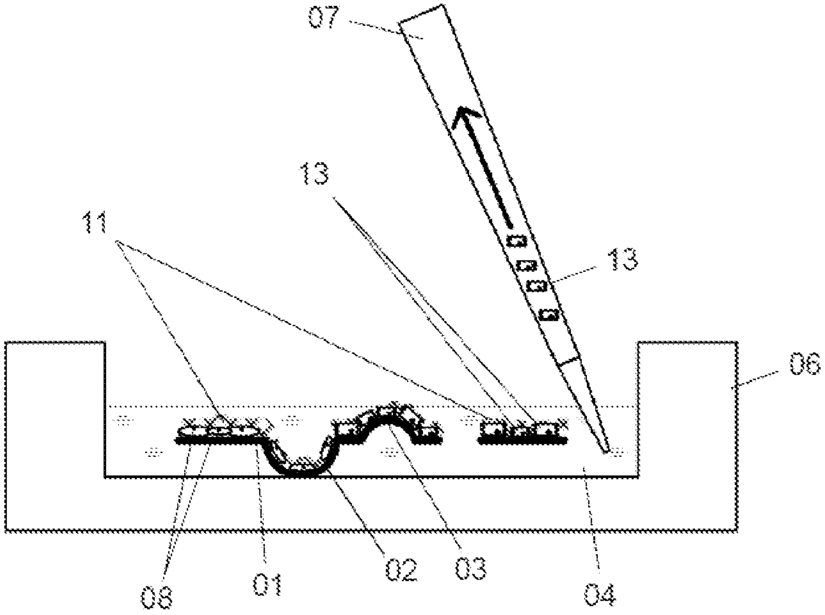
FIG. 6: shows a sixth phase of the first preferred embodiment of the method according to the invention.

FIG. 6 shows a sixth phase of the first preferred embodiment of the method for the reproduction of biological tissue according to the invention. In this sixth phase, the primary cells 13 of the second cell type that are not adhered by the substance 11 are removed from the substrate 01 and from the medium 04 using the pipette 07.

Figure 7:
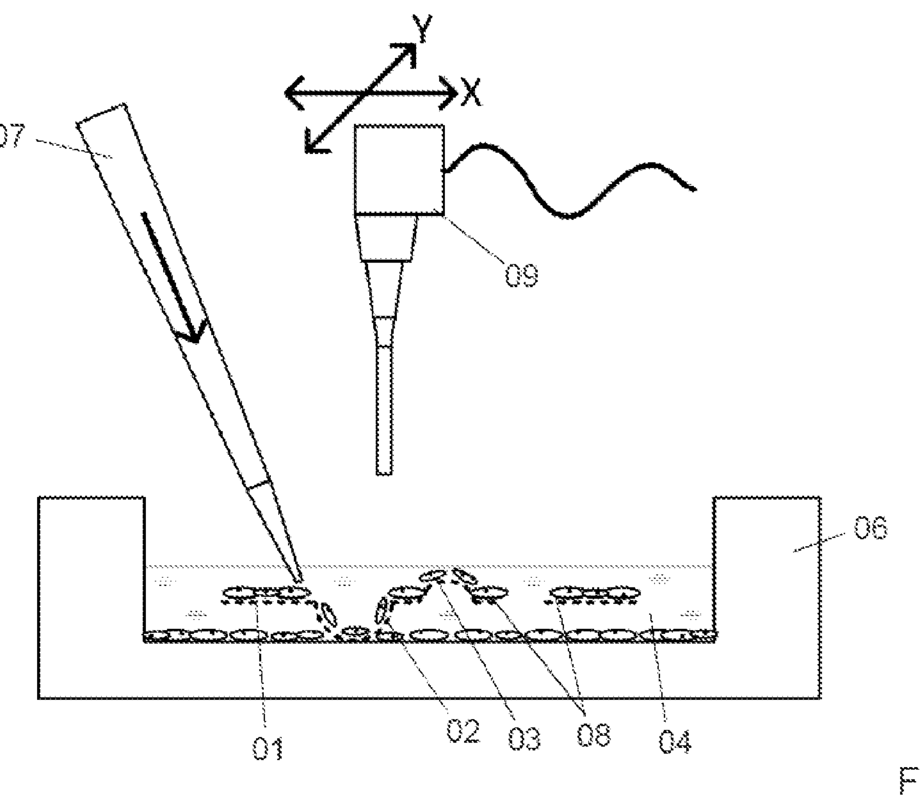
FIG. 7: shows a first phase of a second preferred embodiment of the method according to the invention for reproduction of biological tissue.

FIG. 7 shows a first phase of a second preferred embodiment of the method for the reproduction of biological tissue according to the invention. This second embodiment is initially similar to the first embodiment illustrated in FIGS. 1 to 6. In contrast to the first embodiment, in the second embodiment the substrate 01 is porous. The sequence of the first phase of the second embodiment is similar to the sequence of the first phase of the first embodiment shown in FIG. 1.

Figure 8:
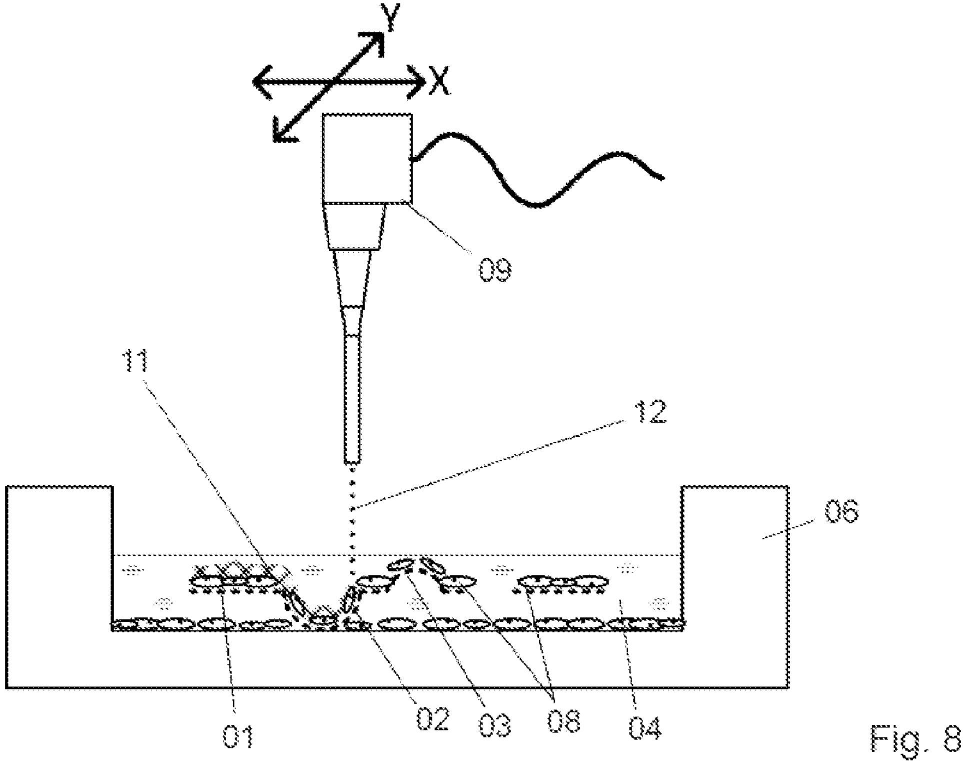
FIG. 8: shows a second phase of the second preferred embodiment of the method according to the invention.

FIG. 8 shows a second phase of the second preferred embodiment of the method for the reproduction of biological tissue according to the invention. The sequence of the second phase of the second embodiment is similar to the sequence of the second phase of the first embodiment shown in FIG. 2.

Figure 9:
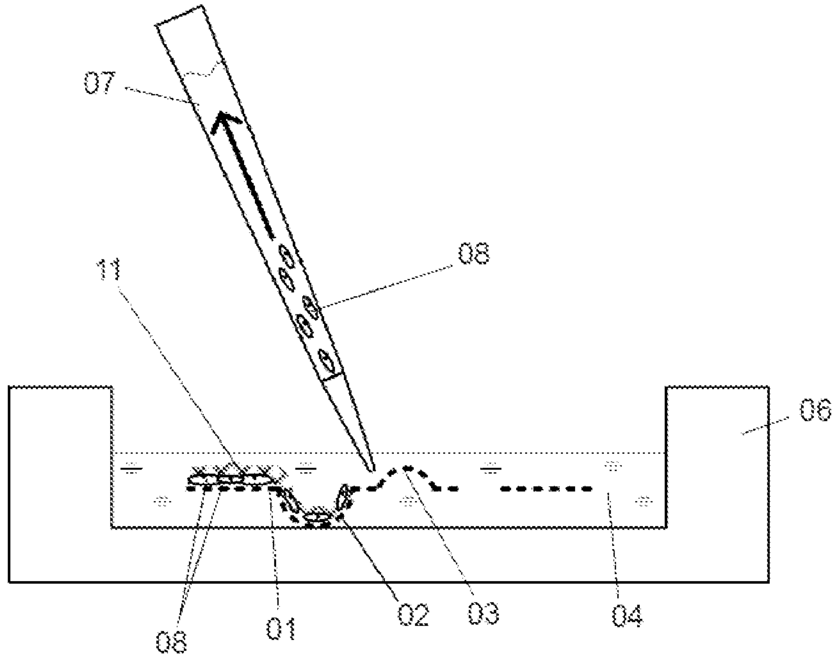
FIG. 9: shows a third phase of the second preferred embodiment of the method according to the invention.

FIG. 9 shows a third phase of the second preferred embodiment of the method for reproduction of biological tissue according to the invention. The sequence of the third phase of the second embodiment is similar to the sequence of the third phase of the first embodiment shown in FIG. 3.

Figure 10:
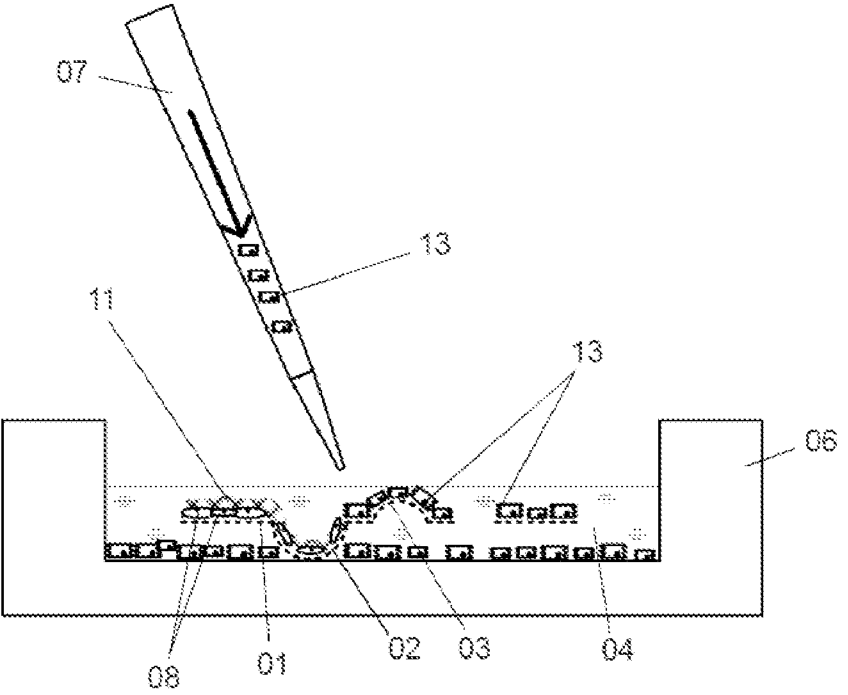
FIG. 10: shows a fourth phase of the second preferred embodiment of the method according to the invention.

FIG. 10 shows a fourth phase of the second preferred embodiment of the method for the reproduction of biological tissue according to the invention. The sequence of the fourth phase of the second embodiment is similar to the sequence of the fourth phase of the first embodiment shown in FIG. 4.

Figure 11:
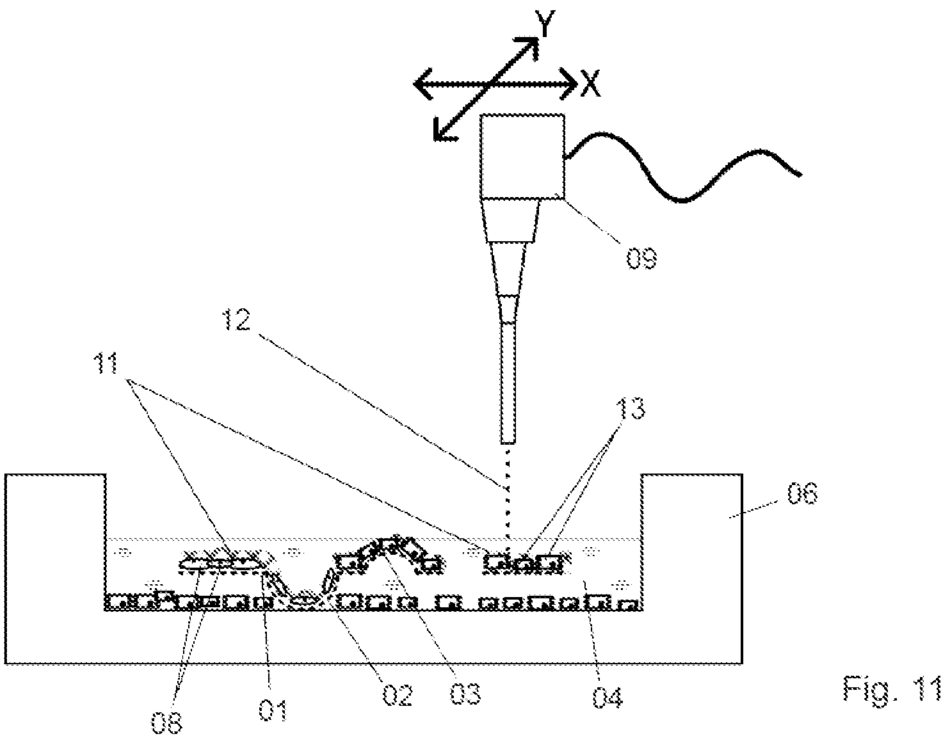
FIG. 11: shows a fifth phase of the second preferred embodiment of the method according to the invention.

FIG. 11 shows a fifth phase of the second preferred embodiment of the method for the reproduction of biological tissue according to the invention. The sequence of the fifth phase of the second embodiment is similar to the sequence of the fifth phase of the first embodiment shown in FIG. 5.

Figure 12:
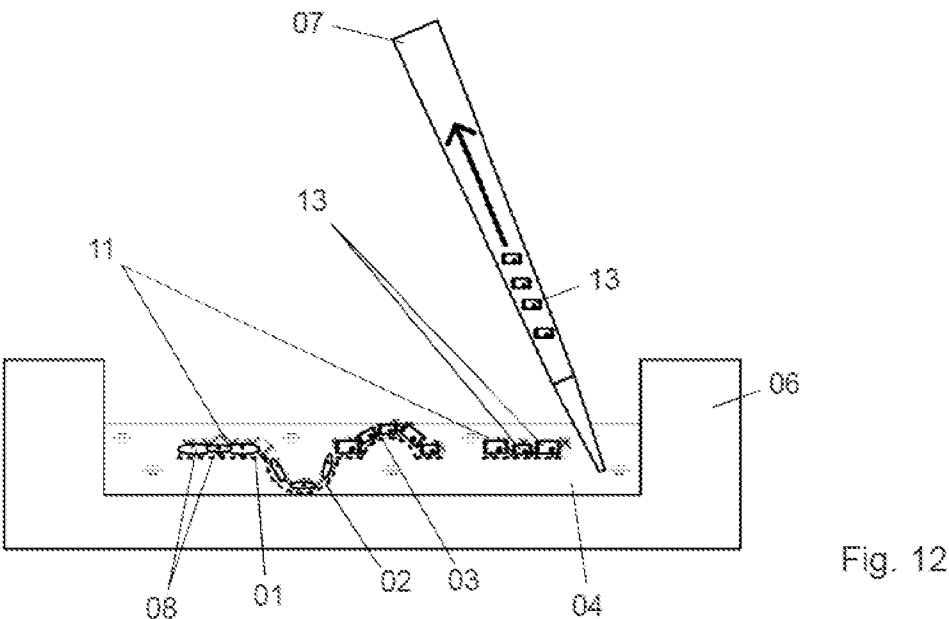
FIG. 12: shows a sixth phase of the second preferred embodiment of the method according to the invention.

FIG. 12 shows a sixth phase of the second preferred embodiment of the method for the reproduction of biological tissue according to the invention. The sequence of the sixth phase of the second embodiment is similar to the sequence of the sixth phase of the first embodiment shown in FIG. 6.

REFERENCE LIST

01 Substrate
02 Cavity
03 Elevation
04 Medium
05 -
06 Machining tray
07 Pipette
08 Primary cells of a first cell type
09 Movable dispensing system
10 -
11 Substance adhering the primary cells
12 Second precursor
13 Primary cells of a second cell type

The invention claimed is:

1. A method for applying a substance (11) that is created through bringing together a first precursor and a second precursor, wherein the substance (11), once created, is capable of adhering cells, the method comprising the steps of:

provision of a substrate (01);

deposit of primary cells (08) of a cell type on the substrate (01); arrangement of the first precursor of the substance (11) adhering the cells (08, 13) on at least a selection of the primary cells (08) of the cell type; and arrangement in a locally targeted manner of the second precursor (12) of the substance (11) adhering the cells (08, 13) to the selection of primary cells (08) of the cell type according to a structure formed by cells of the cell type in a tissue to be reproduced, whereby the first precursor and the second precursor (12) react with each other to form the substance (11) adhering the cells (08, 13), which substance adheres the selection of primary cells (08) of the cell type according to the structure formed by the cells of the cell type in the tissue to be reproduced and forms a first layer of the primary cells (08)

such that the selection of primary cells (08) of the cell type constitutes a reproduction of at least a first section of the biological tissue to be reproduced.

2. The method according to claim 1, wherein the substrate (01) to be provided has microfluidic structural elements.

3. The method according to claim 1, wherein the primary cells (08) of the cell type are stochastically distributed on the substrate (01).

4. The method according to claim 1, wherein the arrangement of the first precursor of the substance (11) adhering the cells (08, 13) on the selection of the primary cells (08) of the cell type is carried out with a locally metering dispensing system (09).

5. The method according to claim 4, wherein the locally metering dispensing system (09) is formed by a dispenser or pipetting system movable in the x-y-z axes.

6. The method according to claim 4, wherein the second precursor (12) is arranged in individual drops at or on the selection of primary cells (08) of the first-cell type, wherein the drops contain at most 5 picoliters of the second precursor (12).

7. The method according to claim 4, wherein during the arrangement in a locally targeted manner of the second precursor (12) with the locally metering dispensing system (09), travel paths are covered in all three spatial axes, wherein the travel paths are at least 10 mm.

8. The method according to claim 1, wherein the substance (11) adhering the cells (08, 13) is formed by a two-component hydrogel, wherein the first precursor constitutes a first component of the two-component hydrogel and the second precursor (12) constitutes a second component of the two-component hydrogel.

9. The method according to claim 1, wherein one of the two precursors (12) comprises an ionotropic polymer formed by alginate, pectin, poly (galacturonate), carrageenan, dextran, gellan, scleroglucan, chitosan, polyphosphazene, sodium polyacrylate and/or polyamino acid.

10. The method according to claim 1, wherein the deposit of the primary cells (08) of the cell type takes place in a medium (04).

11. The method according to claim 10, wherein the medium (04) comprises at least one nutrient medium for the primary cells (08) of the cell type.

12. The method according to claim 10, wherein the medium (04) further comprises the first precursor of the substance (11) adhering the cells (08, 13), or that the first precursor of the substance (11) adhering the cells (08, 13) is mixed into the medium (04) located on the substrate (01).

13. The method according to claim 1, wherein after the first precursor and the second precursor (12) have formed the substance (11) adhering the cells (08, 13), the primary cells (08) of the cell type not belonging to the selection are removed from the substrate (01).

14. The method according to claim 1, further comprising the following steps:

deposit of further primary cells (08) of the cell type on the already formed reproduction of the first section of the biological tissue;

arrangement of the first precursor of the substance (11) adhering the cells (08, 13) on at least a selection of the further primary cells (08) of the cell type; and arrangement in a locally targeted manner of the second precursor (12) of the substance (11) adhering the cells (08, 13) to the selection of the further primary cells (08) of the cell type according to the structure formed by cells of the cell type in the tissue to be reproduced, whereby the first precursor and the second precursor (12) react with each other and form the substance (11) adhering the cells (08, 13), which substance adheres the selection of the further primary cells (08) of the cell type according to the structure formed by the cells of the cell type in the tissue to be reproduced, such that the selection of the further primary cells (08) of the cell type constitutes a reproduction of a further section of the biological tissue to be reproduced.

15. The method according to claim 1, further comprising the following steps:

deposit of primary cells (13) of an additional cell type on the substrate (01) and/or on the already formed reproduction of the first section of the biological tissue;

arrangement of the first precursor of the substance (11) adhering the cells (08, 13) on at least a selection of the primary cells (13) of the additional cell type; and arrangement in a locally targeted manner of the second precursor (12) of the substance (11) adhering the cells (08, 13) to the selection of primary cells (13) of the second additional cell type according to a structure formed by cells of the additional cell type in the tissue to be reproduced, whereby the first precursor and the second precursor (12) are amalgamated and form the substance (11) adhering the cells (08, 13), which substance adheres the selection of the primary cells (13) of the additional cell type according to the structure formed by the cells of the additional cell type in the tissue to be reproduced, such that the selection of the primary cells (13) of the additional cell type constitutes a reproduction of a further section of the biological tissue to be reproduced.

* * * * *